US008953813B2

(12) United States Patent
Loeda

(10) Patent No.: US 8,953,813 B2
(45) Date of Patent: Feb. 10, 2015

(54) REDUCED DELAY DIGITAL ACTIVE NOISE CANCELLATION

(75) Inventor: Sebastian Loeda, Edinburgh (GB)

(73) Assignee: Dialog Semiconductor GmbH, Kirchheim/Teck-Nabern (DE)

(*) Notice: Subject to any disclaimer, the term of this patent is extended or adjusted under 35 U.S.C. 154(b) by 697 days.

(21) Appl. No.: 12/928,869

(22) Filed: Dec. 21, 2010

(65) Prior Publication Data

US 2012/0140942 A1 Jun. 7, 2012

(30) Foreign Application Priority Data

Dec. 1, 2010 (EP) ..................................... 10015174

(51) Int. Cl.

*A61F 11/06* (2006.01)
*G10K 11/178* (2006.01)
*G10K 11/16* (2006.01)
*G10L 21/0208* (2013.01)

(52) U.S. Cl.

CPC .... *G10K 11/1782* (2013.01); *G10K 2210/1081* (2013.01); *G10K 2210/3051* (2013.01); *G10L 21/0208* (2013.01)

USPC ....................................... 381/71.11; 381/71.6

(58) Field of Classification Search

USPC ............. 381/71.6, 71.8, 71.11, 108, 71.1, 74; 704/500; 455/63.1; 375/240.15–240.17, 240.29; 379/398, 379/414

See application file for complete search history.

(56) References Cited

U.S. PATENT DOCUMENTS

| | | | |
|---|---|---|---|
| 5,251,262 | A | 10/1993 | Suzuki et al. |
| 5,917,919 | A | 6/1999 | Rosenthal |
| 6,078,672 | A | 6/2000 | Saunders et al. |
| 6,278,786 | B1 | 8/2001 | McIntosh |
| 6,418,227 | B1 | 7/2002 | Kuo |
| 6,898,290 | B1 | 5/2005 | Saunders et al. |
| 7,110,551 | B1 | 9/2006 | Saunders et al. |

(Continued)

FOREIGN PATENT DOCUMENTS

WO WO 2008/155725 12/2008

OTHER PUBLICATIONS

European Search Report—App. No. 10015174.5-1224, Mail date—Jul. 27, 2011, Dialog Semiconductor GmbH.

*Primary Examiner* — Vivian Chin
*Assistant Examiner* — Ammar Hamid
(74) *Attorney, Agent, or Firm* — Saile Ackerman LLC; Stephen B. Ackerman

(57) ABSTRACT

A digital active noise cancellation circuit device (330) includes an oversampled, sigma-delta, A/D converter (204), a digital decimation filter (208), a digital intermediate filter (308), a digital interpolation filter (232), and a sigma-delta, D/A converter (252). The device (330) is operative to perform the steps of: receiving (904) the analog noise signal (64), converting (908) the analog noise signal into a digital noise signal (261); transferring (912) the digital noise signal to a digital decimation filter, selectively bypassing (916) at least a portion of the digital decimation filter by transferring the digital noise signal to a digital intermediate filter (304), processing (920) the digital noise signal in the digital intermediate filter to generate a digital anti-noise signal (316), transferring (1010) the digital anti-noise signal into a digital interpolation filter (232) operable to up-sample the digital anti-noise signal, selectively bypassing (1020) at least a portion of the digital interpolation filter and converting (1030) the digital anti-noise signal into an analog anti-noise signal (68).

31 Claims, 10 Drawing Sheets

(56) References Cited

U.S. PATENT DOCUMENTS

| | | | | |
|---|---|---|---|---|
| 7,536,018 | B2 | 5/2009 | Onishi et al. | |
| 2005/0147179 | A1* | 7/2005 | Paoli et al. | 375/295 |
| 2006/0251266 | A1 | 11/2006 | Saunders et al. | |
| 2009/0086990 | A1 | 4/2009 | Christoph | |
| 2010/0014685 | A1 | 1/2010 | Wurm | |
| 2010/0195844 | A1 | 8/2010 | Christoph et al. | |
| 2010/0272280 | A1* | 10/2010 | Joho et al. | 381/71.6 |
| 2011/0222711 | A1* | 9/2011 | Kong et al. | 381/108 |

* cited by examiner

REDUCED DELAY DIGITAL ACTIVE NOISE CANCELLATION

FIELD OF THE INVENTION

The invention relates generally to audio devices and, more particularly, to digital, active noise cancellation circuits for audio devices.

BACKGROUND OF THE INVENTION

Active noise cancellation techniques are well-known in the art. In-ear and circumaural headphones generally exhibit good passive filtering of high-frequency ambient noise. However, this passive filtering is typically not effective for low-frequency (500 Hz or less) ambient noise. Active noise cancellation techniques are well-known as a means for dealing with low-frequency ambient noise in headphones and other audio devices. Generally, active noise cancellation is achieved by measuring the ambient noise and then emitting a copy of the noise signal that has been inverted, or made completely out-of-phase, to thereby cancel the noise signal at the hearing of the listener.

The most common approach used in this area is feed-forward, active cancellation method. Ambient noise is measured, inverted, and then added to the intended audio content in order to attenuate the ambient noise present at the ear drum of the listener. However, in many applications, considerable acoustic and electrical delay between the ambient noise measured and the inverse noise may turn an intended cancelling effect (anti-phase) into an additive effect (in-phase). This delay is particularly a problem for high-frequency ambient noise where the signal phase shift is higher and therefore results in an additive and audible 'whizzing' noise. It is therefore common in the art to filter out the inverted high-frequency ambient noise through a low-pass filter before it is reproduced in the earphone. Further, active, feed-forward noise cancellation is frequently implemented in headphone devices through the use of simple, inverting analog filters to approximate the headphone acoustic response.

Modern, portable low-power audio ICs are becoming fully-integrated, audio devices with digital signal processing (DSP) cores in which all mixing and audio processing is performed digitally. Audio signals, including the measured noise, are first converted into digital signals using high-fidelity analog-to-digital converters (ADC or A/D converters). The digital noise is processed and mixed in the DSP to generate an anti-noise signal, which is then reproduced in analog via a high-fidelity digital-to-analog converter (DAC or D/A converter). Both A/D and D/A converters are typically of the oversampled, sigma-delta (SD) type. These A/D and D/A SD converters achieve high-fidelity conversion with quantization noise-shaping by oversampling the relatively low-frequency audio signal N-times above the Nyquist rate, $f_s$. The A/D converter digital output is later down-sampled from a low-resolution digital word running at N-times $f_s$ to a high-resolution digital word running at $f_s$. The DSP typically runs at this lower sampling rate of $f_s$ to save power. Subsequently, when DSP processing is completed, the high-resolution word running at $f_s$ is converted back to a low-resolution digital word running at M times $f_s$. The digital anti-noise signal is then converted, via D/A converter, back to an analog anti-noise signal.

Prior to DSP processing, the digital noise signal is converted to a higher resolution/lower frequency using a decimation filter. This decimation filter is typically implemented in two stages: (1) a cascaded integrator-comb CIC filter and (2) a chain of finite-impulse response (FIR) filters. The CIC filter down-samples the data words running at N times $f_s$ to an intermediate multiple of $f_s$ with notches around the aliasing frequencies, while the FIR filters remove any remaining high-frequency quantization noise introduced by the SD ADC. After DSP processing, the digital anti-noise signal is converted to a lower resolution/higher frequency using an interpolation filter. The interpolation filter typically consists of a cascade of FIR filters, followed by an up-sampler (e.g., a zero-stuffer or a zero-order hold). The FIR filters remove the up-sampled images of the signal bandwidth that would otherwise fold around the aliasing frequencies at the output of the D/A converter. The number of filtering stages required at either end (i.e., decimation or interpolation) depends on the oversampling ratio (OSR) and the order of quantization noise shaping of the SD converter.

Unfortunately, the decimation filtering and interpolation filtering necessary to perform the anti-noise signal processing in the DSP introduces large signal processing delays. These delays make the DSP core audio code architecture unsuitable for feed-forward active noise cancellation. An analog bypass path may be used to bypass the decimation and interpolation filtering steps. However, the use of an analog bypass path is expensive in terms of device complexity, area, and power.

It is therefore very useful to provide a low delay, digital bypass path to improve active noise cancellation performance. A digital bypass path potentially eliminates the need for a number of FIR filters, CIC filters, up-samplers, and a sigma-delta modulator for a DAC. A digital bypass path makes it possible to implement more complex and accurate filter responses in digital technology to thereby compensate for acoustic effects in forward active noise cancellation. A digital bypass path potentially allows direct trade-off of parameters, such as gain resolution, filter coefficient resolution and complexity, for reduced delay.

BRIEF DESCRIPTION OF THE DRAWINGS

The present invention and the corresponding advantages and features provided thereby will be best understood and appreciated upon review of the following detailed description of the invention, taken in conjunction with the following drawings, where like numerals represent like elements, in which.

DETAILED DESCRIPTION OF THE INVENTION

A method provides improved digital noise cancellation for a digital audio device by, among other things, bypassing part of the digital filtering path to reduce delay in the generation of the anti-noise signal. In an exemplary embodiment of the present invention, a method generates an anti-noise signal for digital active noise cancellation in a digital audio device. An analog noise signal is received and converted to a digital noise signal by an oversampled, sigma-delta, A/D converter. The digital noise signal is transferred, first, to a digital decimation filter and, then, to a digital intermediate filter after a portion of the digital decimation filter is selectively bypassed. A digital anti-noise signal is generated in the digital intermediate filter.

In another exemplary embodiment of the present invention, a digital audio device is enabled for active noise cancellation. A digital anti-noise circuit is coupled to a digital audio circuit. The digital audio circuit is operable to combine a primary output audio signal with the analog anti-noise signal and to amplify the combined signals through a speaker. The digital audio includes an oversampled, sigma-delta, A/D converter, a digital decimation filter, a digital intermediate filter, a digital interpolation filter, and a sigma-delta, D/A converter. The digital anti-noise circuit is operative: to receive and convert an analog noise signal into a digital noise signal by an oversampled, sigma-delta A/D converter; to transfer the digital noise signal, first, to a digital decimation filter and, then, to a digital intermediate filter after a portion of the digital decimation filter is selectively bypassed; to generate a digital anti-noise signal in the digital intermediate filter and then to transfer it to a digital interpolation filter; to selectively bypass a portion of the digital interpolation filter; and to convert the digital anti-noise signal to an analog anti-noise signal by a sigma-delta, D/A converter.

As such, a device and method are disclosed that provides a low delay, digital bypass path to improve active noise cancellation performance in a digital audio circuit. In particular, the low delay, digital bypass path improves active noise cancellation performance. In addition, a digital bypass path potentially eliminates the need for a number of FIR filters, CIC filters, up-samplers, and a sigma-delta modulator for a D/A converter. Further, a digital bypass path makes it possible to implement more complex and accurate filter responses in digital technology to thereby compensate for acoustic effects in forward active noise cancellation. A digital bypass path also potentially allows direct trade-off of parameters, such as gain resolution, filter coefficient resolution, and complexity, for reduced delay. Other advantages will be recognized by those of ordinary skill in the art.

Figure 1:
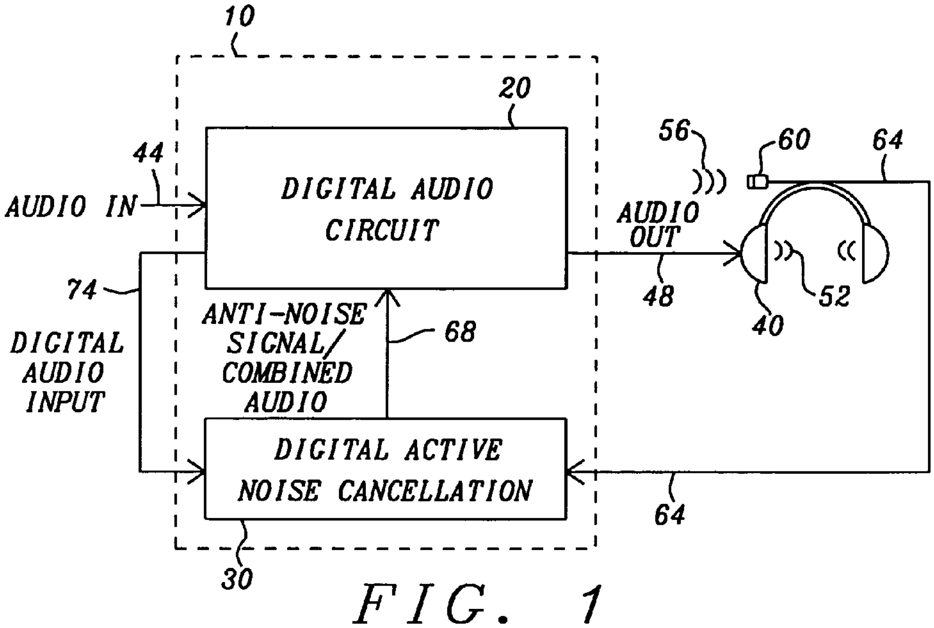
FIG. 1 is a schematic block diagram of a digital audio device enabled for active noise cancellation in accordance with one embodiment of the invention.

FIG. 1 is a schematic block diagram of a digital audio device 10 enabled for employing one example of an active noise cancellation circuit 30 for an digital audio circuit 20 in accordance with one embodiment of the invention. The digital audio device 10 includes a digital audio circuit 20 and a digital active noise cancellation circuit 30. The digital audio device 10 may be any suitable digital device with audio functionality including, but not limited to, a cellular telephone, an internet appliance, a laptop computer, a palmtop computer, a personal digital assistant, a digital entertainment device, a radio communication device, a mobile music playing device, a tracking device, a personal training device, or a combination thereof.

The digital audio circuit 20 is capable of receiving an audio input signal 44, generating an audio output signal 48, and amplifying this audio output signal 48 through a speaker device 40. The digital audio circuit 20 may be any digital circuit suitable for processing the audio input 44 to a suitable digital representation as is known in the art. The digital audio circuit may be a digital signal processor (DSP), microcontroller, central processing unit, baseband processor, co-processor, or any suitable processing device. In addition it may be discrete logic, or any suitable combination of hardware, software or firmware, or a non-processor, digital circuit. The speaker device 40 is shown as a headphone. The speaker device 40 could be an in-ear headphone or, as shown, a circumaural headphone. Alternatively, the speaker device 40 could be of a non-headphone type. The analog audio output signal 48 is emitted from the speaker device 40 as audio sound 52.

The combination of the digital audio circuit 20, speaker device 40, and digital active noise cancellation circuit 30 are configured to enable active, feed-forward noise cancellation. In particular, a microphone means 60 is included with, or integrated within, or located near the speaker device 40 such that the ambient noise 56 near the speaker 40 may be measured and transmitted as an analog noise signal 64. A variety of microphones, such as condenser microphones and piezoelectric sensors, may be used for the microphone means as will apparent to one skilled in the art. Alternatively, a digital microphone with a built-in sigma-delta, A/D converter may be used. In such a case, the sigma-delta, A/D converter 204 shown in FIG. 2 would not be needed since the digital microphone would generate a digital bit-stream. Referring again to FIG. 1, the ambient noise 56 is preferably measured in a way that isolates the measurement from the audio sound 52 such that the audio sound 52 is either not included, or only very minimally included, in the resulting analog noise signal 64 generated by the microphone means 60.

The analog noise signal 64 is received and processed by the digital active noise cancellation circuit 30. The digital active noise cancellation circuit 30 is capable to receive the analog noise signal 64, to process this signal, and to output an anti-noise signal 68 according to features further described below. The analog anti-noise signal 68 is an analog representation of the analog noise signal 64 after it has been inverted or caused to be 180 degrees out of phase. The anti-noise signal 68 is provided to the digital audio circuit 20 which, in addition to its above-listed functions, also is capable of combining the anti-noise signal 68 with the audio in signal 44. It is the combination of the primary audio signal 44 and the analog anti-noise signal 68 that is amplified though the speaker device 40 as the audio output signal 48.

As an important alternative feature, the digital audio circuit 20 may provide a digital audio input signal 74, as shown, to the digital active noise cancellation circuit 30. This digital audio input signal 74 may be combined with a digital anti-noise signal within the digital active noise cancellation circuit 30 to create a combined audio signal 68 rather than an anti-noise signal.

While the audio circuit device 10 appears at first glance to use feedback, in fact a feed-forward scheme is used. The ambient noise 56 is measured as the analog noise signal 64 and is separated from the audio sound 52. The analog noise signal 64, once converted to a analog anti-noise signal 68, is fed into primary audio path in digital audio circuit 20. The scheme does not measure the audio output 52 nor attempt to drive a noise component in the audio output (or an error signal based on such a noise component) to zero via feedback. Rather, the inverse ambient noise is added, via the analog anti-noise signal 68, to the primary audio output in the forward path.

Figure 2:
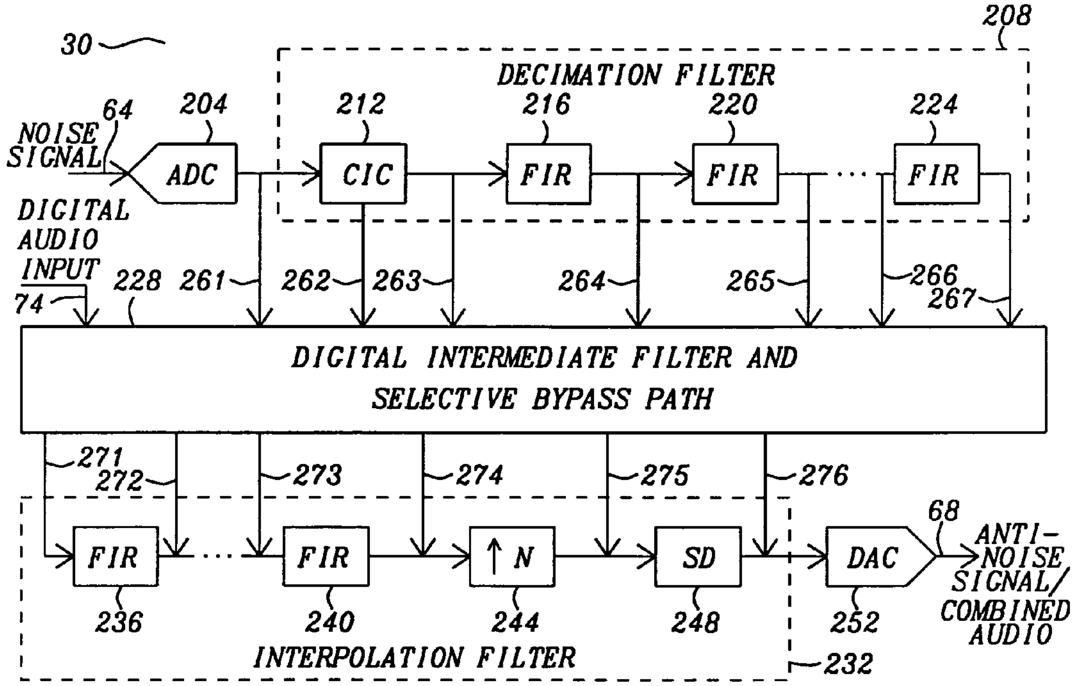
FIG. 2 is a schematic block diagram of a digital active noise cancellation circuit device in accordance with one embodiment of the invention.

FIG. 2 is schematic block diagram of a digital active noise cancellation circuit 30 in accordance with one embodiment of the invention. The novel digital active noise cancellation circuit 30 is shown in its most general form. The digital active noise cancellation circuit 30 includes an oversampled, sigma-delta, A/D converter 204, a digital decimation filter 208, a digital intermediate filter 228, a digital interpolation filter 232, and a sigma-delta, D/A converter 252. The circuit 30 is capable to receive the analog noise signal 64 at the input of the A/D converter 204.

The analog noise signal 64 is converted to a digital noise signal 261 by the A/D converter 204. Preferably, the analog noise signal 64 is subjected to oversampling such that A/D converter 204 samples the signal 64 at a rate at least N-times greater than the sampling frequency, $f_s$, required to satisfy the Nyquist rate. More preferably, the A/D converter is a delta-sigma, A/D converter using at least one integrator and comparator. The result is a bit stream, at the oversampled rate of N-times $f_s$, representing the noise signal in digital form. This digital noise signal 261 has a low resolution but a high frequency.

The decimation filter 208 is next in the signal path. The decimation filter is actually a chain of filters, including a cascaded integrator-comb (CIC) filter 212 and a series of finite-impulse response (FIR) filters 216, 220, and 224. As shown in the illustration, the FIR filters 216, 220, and 224, may include many more filter stages than the number shown. Conversely, fewer FIR filters stages may be used. The purpose of the decimation filter 208 is to down-sample the digital noise signal 261 from the high frequency rate of N-times $f_s$ to a frequency, such as $f_s$, or simply a lower multiple of $f_s$, that can be further digitally processed with circuits at a lower clocking rate. For example, if the digital noise signal were to be processed in a DSP or other circuit that operates at $f_s$, then the decimation filter 208 would need to completely down-sample to that frequency. During decimation, or down-sampling, the digital noise signal 261 bit stream is sampled at the desired, lower frequency rate. At each sample time, the average digital value is taken and held. The resulting decimation filter output signal 267 is of higher resolution than the original digital noise signal 261 but of lower frequency.

The FIR filters 216, 220, and 224 are a type of discrete-time filter. Each filter's impulse response is said to be finite because the output settles to zero in a finite number of sample intervals. The CIC filter 212 is a special type of FIR filter that combines discrete-time filtering with a decimation function. The CIC filter 212 may be implemented as one or more cascaded integrators, a down-sampler, and one or more comb sections. As the digital noise signal 261 is processed through the CIC filter 212, the high frequency data (N-times $f_s$) is down-sampled to an intermediate multiple of $f_s$ with notches around the aliasing frequencies. The FIR filters 216, 220, and 224 filter out the remaining quantization noise introduced by the sigma-delta A/D converter 204.

As an important feature of the present invention, the digital noise signal output 261 of the A/D converter is available for transfer directly into a digital intermediate filter and selective bypass path circuit 228, or simply the digital intermediate filter, 228. In addition, the output 263 of the CIC filter 212 and the outputs 262 of CIC filter 212 internal stages, are available for the digital intermediate filter 228. Further, the outputs 264, 265, 266, and 267, of each of the FIR filters 216, 220, and 224 are available at the digital intermediate filter 228. The availability of intermediate outputs of the digital noise signal from each of the stages of the decimation filter 208 (from the A/D output 216 through the last FIR filter output 267) enables selective bypassing of at least a part of the digital decimation filter 208. The digital intermediate filter 228 may be implemented in a variety of ways to achieve a variety of bypassing schemes as will be shown below.

An interpolation filter 232 follows the digital intermediate filter 228 in the signal path for the digital noise signal 261. As with the decimation filter 208, access is provided to the anti-noise signal at each stage within the digital interpolation filter 232. Therefore, the selective bypassing of at least a part of the digital interpolation filter 232 is enabled. The digital interpolation filter 232 includes a cascade of FIR filters 236 and 240, an up-sampler 244, and a sigma-delta modulator 248. The FIR filters 236 and 240 are useful for filtering out up-sampled images of the signal bandwidth that would otherwise fold around the aliasing frequencies at the output 68 of the D/A converter 252. The up-sampler 244 may be in the form of a zero-stuffier or a zero-order hold. The up-sampler 244 increases the frequency of the digital noise signal 274 up to the desired output rate (generally, M-times $f_s$). The sigma-delta modulator 248 is used to improve the accuracy of the subsequent D/A converter 252, typically using an integrator, a quantizer, and error feedback. The D/A converter 252 is a sigma-delta type using at least one integrator and a comparator. Overall, the D/A converter shapes and spreads out quantization noise.

If the entire path in the digital noise cancellation circuit 30 is used, then the analog noise signal 64 is converted to a high frequency, low resolution digital noise signal 261 by the D/A converter. The digital noise signal 261 is then decimated and filtered completely to create a low frequency, high resolution digital noise signal 267 that is presented to the digital intermediate filter 228. The digital intermediate filter 228 inverts the digital noise signal 267 to produce a digital anti-noise signal 271. Again, if the entire interpolation filter 232 is used, then the digital anti-noise signal 271 is completely filtered, up-sampled, and sigma-delta modulated to create the interpolated and sigma-delta, digital noise signal 276. This signal 276 is then converted to an analog anti-noise signal by the D/A converter 252.

If the entire signal path of the digital active noise cancellation circuit is followed, then significant signal delay is introduced. This signal delay causes problems with high frequency noise components and is unsuitable for feed-forward active noise cancellation. However, as an important feature of the present invention, the novel digital noise cancellation circuit 30 enables selective bypass of all or part of the decimation or interpolations paths. The selective bypass capability creates a faster, more responsive signal path that enables active noise cancellation of even high frequency noise. In general, any decimation filter stage may be bypassed to any interpolation filter stage depending on (1) N and M, where the analog noise signal is sampled at N-times $f_s$ and the digital anti-noise signal is converted at M-times $f_s$, (2) the sigma-delta modulators, and (3) the tradeoff between delay and digital word resolution.

The digital intermediate filter 228 may implement any filter response required for the active noise cancellation, in addition to any decimation and interpolation filtering. The digital intermediate filter 228 may be a digital signal processor (DSP), microcontroller, central processing unit, baseband processor, co-processor, or any suitable processing device. In addition it may be discrete logic, or any suitable combination of hardware, software or firmware or any non-processor, digital circuit. The sampling frequencies of the digital noise signal 261 and of the digital anti-noise signal 276 need not be the same. However, as will be described in the embodiments shown in FIGS. 3-8 below, these additional capabilities bring unique tradeoffs.

As an important alternative, a digital audio input 74 may be provided to the digital intermediate filter 228. The digital intermediate filter 228 may then combine the digital audio input 74 with the generated digital anti-noise signal such that the digital intermediate filter 228 output signal 271, 272, 273, 274, 275, or 276, is actually a digital combined audio signal rather than just a digital anti-noise signal.

Figure 3:
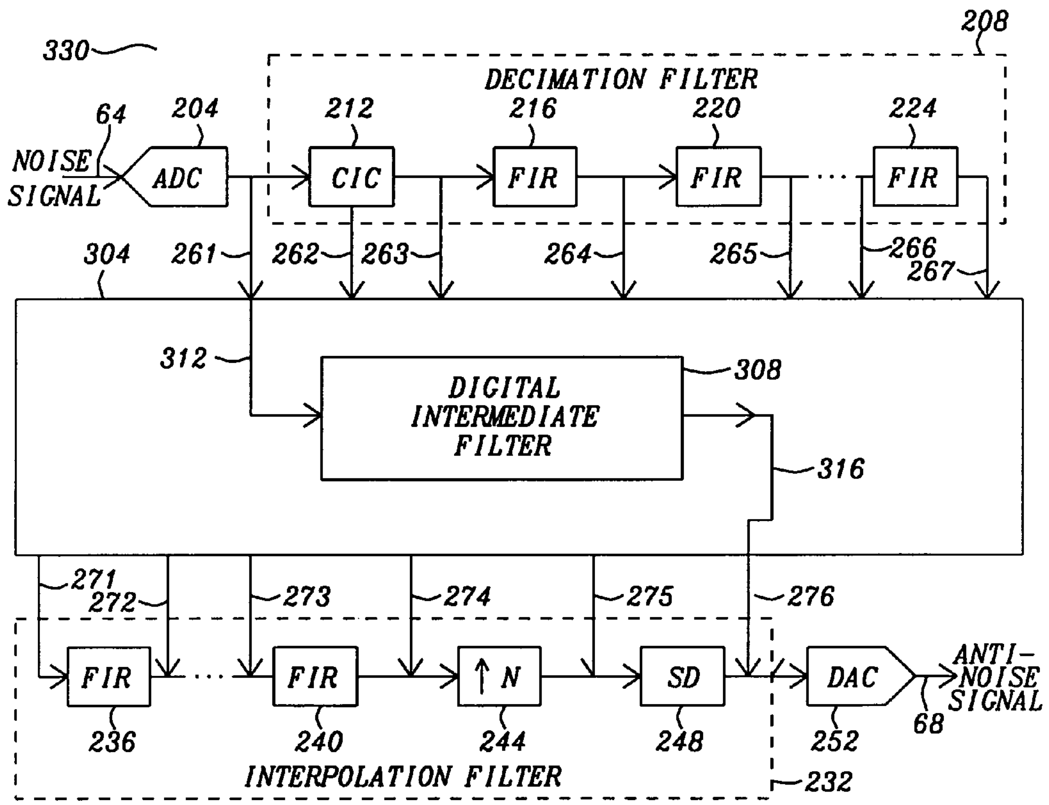
FIG. 3 is a schematic block diagram of a digital active noise cancellation circuit device in accordance with one embodiment of the invention.

FIG. 3 is a schematic block diagram of a digital active noise cancellation circuit 330 in accordance with one embodiment of the invention. Here, the digital intermediate filter and bypass path 304 is configured to provide a bypass 312 for the output signal 261 of the A/D converter 204 to the digital intermediate filter 308. Another bypass 316 is provided for the output 316 of the digital intermediate filter 308 to pass to the input 276 of the D/A converter 252. This configuration introduces the minimum amount of delay between the input analog noise signal 64 and the output analog anti-noise signal 68. A minimum delay improves the ability for the active noise cancellation circuit to properly cancel high frequency noise. However, the possible digital intermediate filter implementations are limited to using the low resolution and high frequency of the digital noise signal 261 coming from the A/D converter 204. In addition, the sampling rates for the A/D converter 204 and D/A converter 252 must be the same (N=M). Further, if the word size of the digital anti-noise signal 276 at the input to the D/A converter 252 is smaller than that of the digital noise signal 261 at the output of the A/D converter 204, then some signal resolution will be lost.

Figure 4:
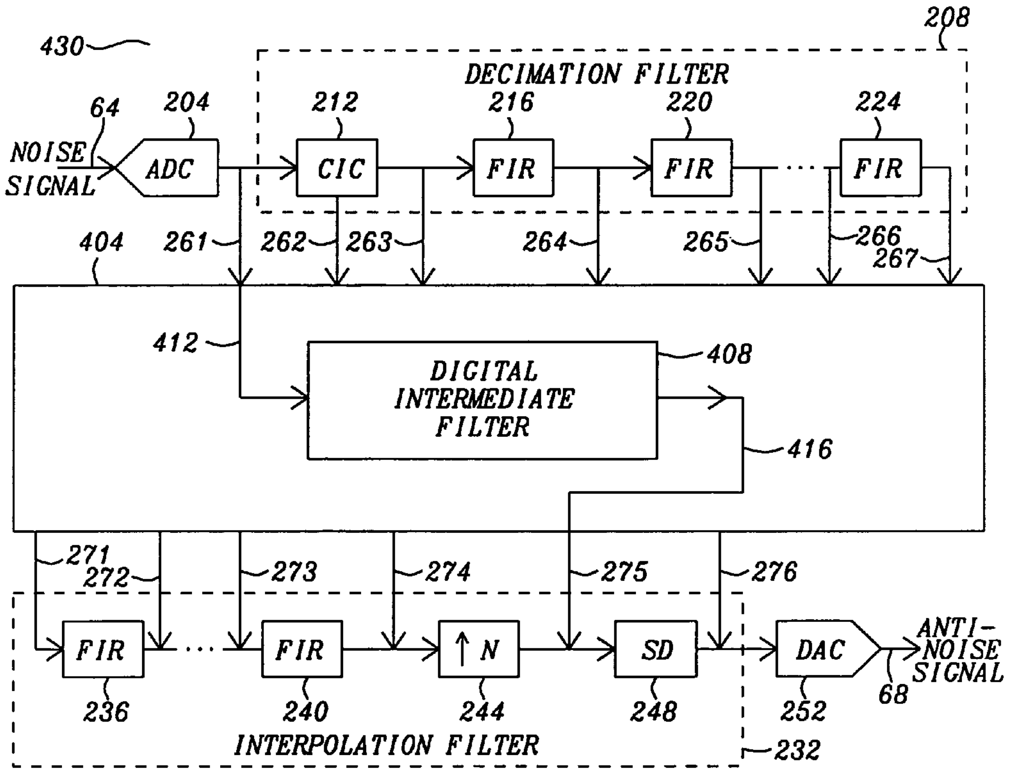
FIG. 4 is a schematic block diagram of a digital active noise cancellation circuit device in accordance with one embodiment of the invention.

FIG. 4 is a schematic block diagram of a digital active noise cancellation circuit 430 in accordance with one embodiment of the invention. Here, the digital intermediate filter and bypass path 404 is configured to provide a bypass 412 for the output signal 261 of the A/D converter 204 to the digital intermediate filter 408. However, the second bypass 416 is provided for the output 416 of the digital intermediate filter 408 to pass to the input 275 of the sigma-delta modulator 248. This configuration introduces slightly more delay between the input analog noise signal 64 and the output analog anti-noise signal 68. However, this configuration will limit the dynamic range of the D/A converter 252 as its incoming sigma-delta modulator 248 must now include high-frequency quantization noise from the A/D converter 204 as well as that present in the noise signal.

Figure 5:
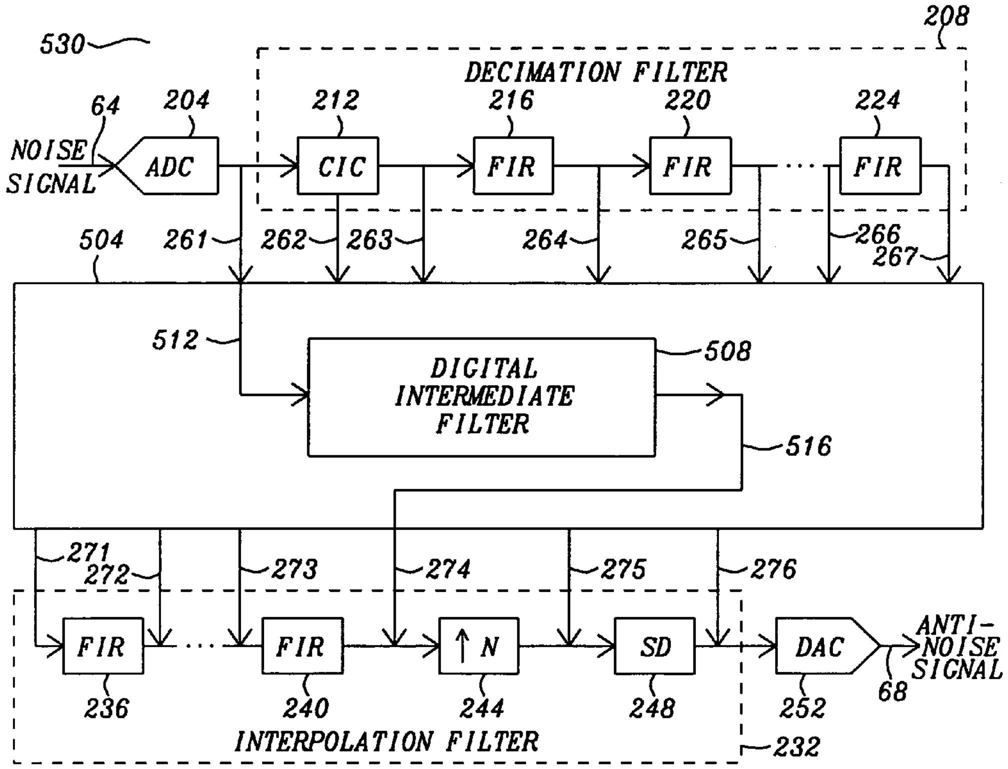
FIG. 5 is a schematic block diagram of a digital active noise cancellation circuit device in accordance with one embodiment of the invention.

FIG. 5 is a schematic block diagram of a digital active noise cancellation circuit 530 in accordance with one embodiment of the invention. Here, the digital intermediate filter and bypass path 504 is configured to provide a bypass 512 for the output signal 261 of the A/D converter 204 to the digital intermediate filter 508. However, the second bypass 516 is provided for the output 516 of the digital intermediate filter 508 to pass to the input 274 of the sigma-delta modulator 244. This configuration introduces slightly more delay between the input analog noise signal 64 and the output analog anti-noise signal 68. However, this configuration will allow the input noise signal oversampling (N) to be less than or equal to the output anti-noise up-sampling (M) before frequency folding occurs.

Figure 6:
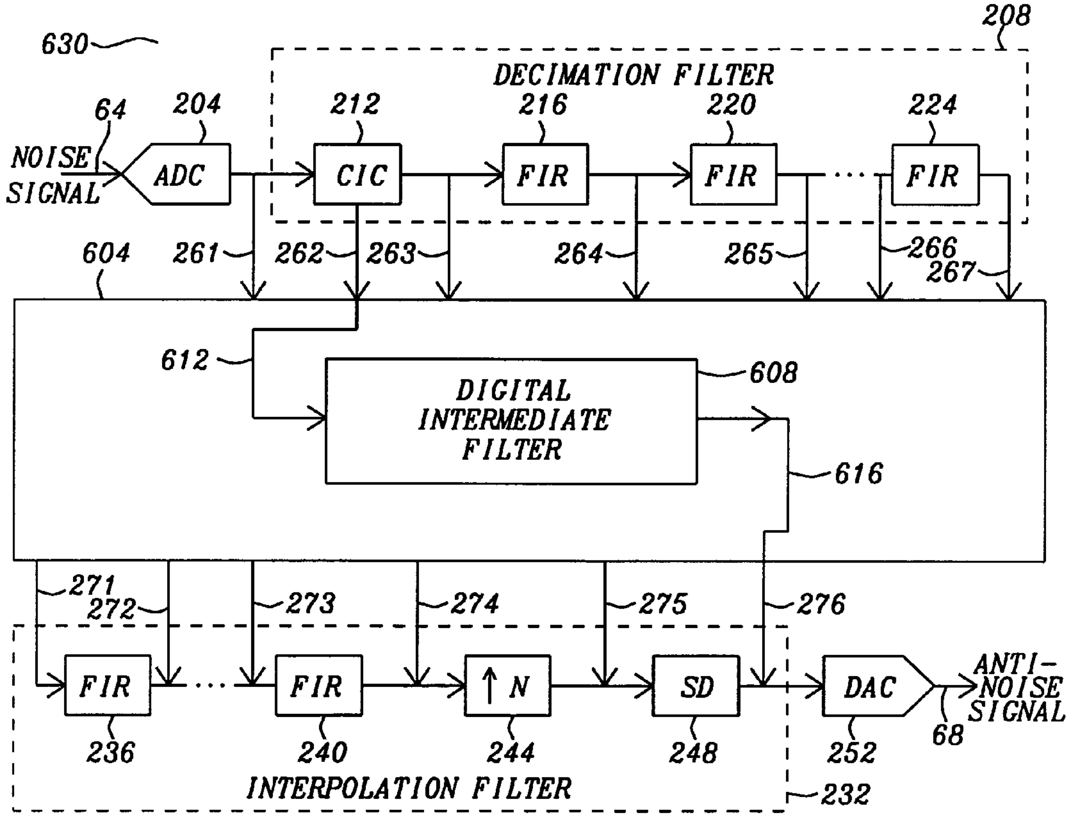
FIG. 6 is a schematic block diagram of a digital active noise cancellation circuit device in accordance with one embodiment of the invention.

FIG. 6 is a schematic block diagram of a digital active noise cancellation circuit 630 in accordance with one embodiment of the invention. Here, the digital intermediate filter and bypass path 604 is configured to provide a bypass 612 for the either the output signal 263, or a stage signal 262 (as shown), of the CIC filter 212 to the digital intermediate filter 608. Alternatively, the bypass 612 may be provided for any of the subsequent FIR filters 216, 220, or 224. However, the second bypass 616 is provided for the output 616 of the digital intermediate filter 608 to pass to the input 276 of the D/A converter 252. This configuration introduces more delay between the input analog noise signal 64 and the output analog anti-noise signal 68 due to the additional signal processing in the input noise signal path. However, this configuration will allow the output anti-noise signal up-sampling rate (M) to be more than the input noise sampling (N) before frequency folding occurs.

Figure 7:
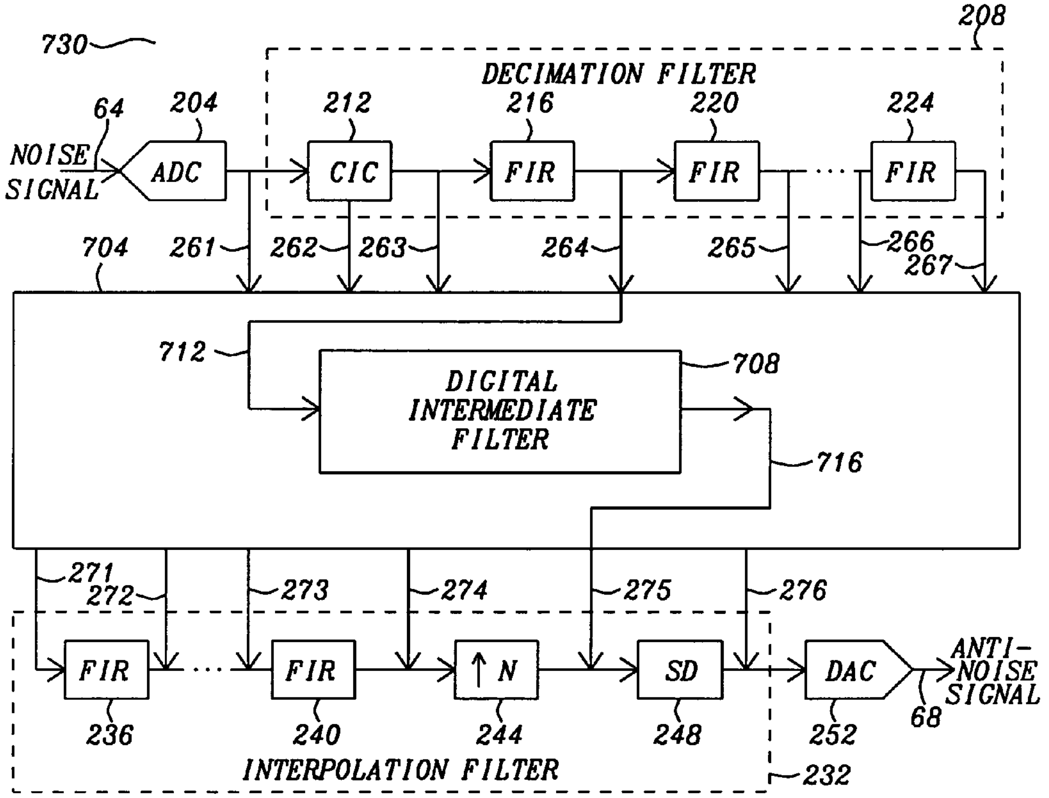
FIG. 7 is a schematic block diagram of a digital active noise cancellation circuit device in accordance with one embodiment of the invention.

FIG. 7 is a schematic block diagram of a digital active noise cancellation circuit 730 in accordance with one embodiment of the invention. Here, the digital intermediate filter and bypass path 704 is configured to provide a bypass 712 for the output 264 of one of the FIR filters 216 to the digital intermediate filter 708 Alternative, the bypass path could be configured to route the output signal 263 of the CIC filter 212 or a stage signal 262 of the CIC filter 212 to digital intermediate filter 708. The second bypass 716 is provided for the output 716 of the digital intermediate filter 708 to pass to the input 275 of the sigma-delta modulator 248.

Figure 8:
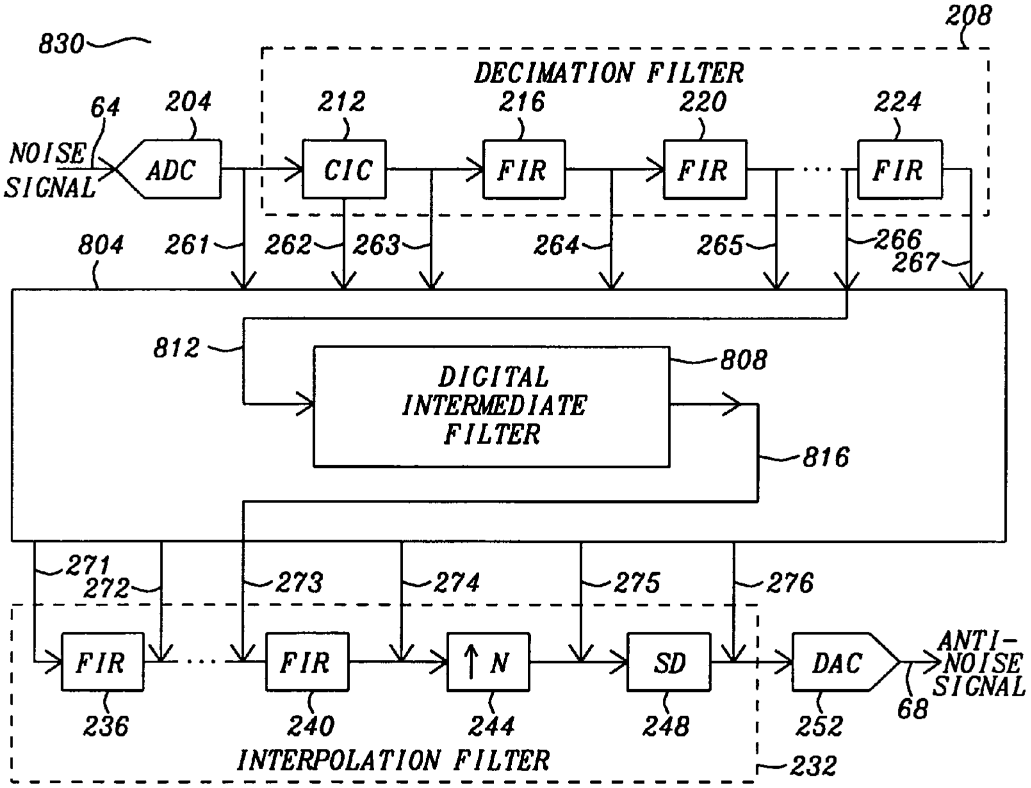
FIG. 8 is a schematic block diagram of a digital active noise cancellation circuit device in accordance with one embodiment of the invention.

FIG. 8 is a schematic block diagram of a digital active noise cancellation circuit 830 in accordance with one embodiment of the invention. Here, in the most general case, any stage 262 or 263 of the CIC filter 212, output 264, 265, 266, or 267, of the FIR filter decimation stages 216, 220, and 224, and any output 272, 273, or 274 of the FIR filter interpolation stage 236 and 240, may be bypassed in order to reduce the delay introduced by the active noise cancellation digital signal processing. The digital intermediate filter and bypass path 804 is configured to provide a bypass 812 for a decimation filter stage signal 266 to the digital intermediate filter 808. The second bypass 816 is provided for the output 816 of the digital intermediate filter 808 to pass to an input 273 of an interpolation filter stage. The reduced delay may be carefully traded off for digital resolution and complexity in the digital intermediate filter 808 implementation. Some combinations will yield frequency folding. Other combinations will limit dynamic range, over-sampling ratio (OSR), and sigma-delta noise shaping.

Figure 9:
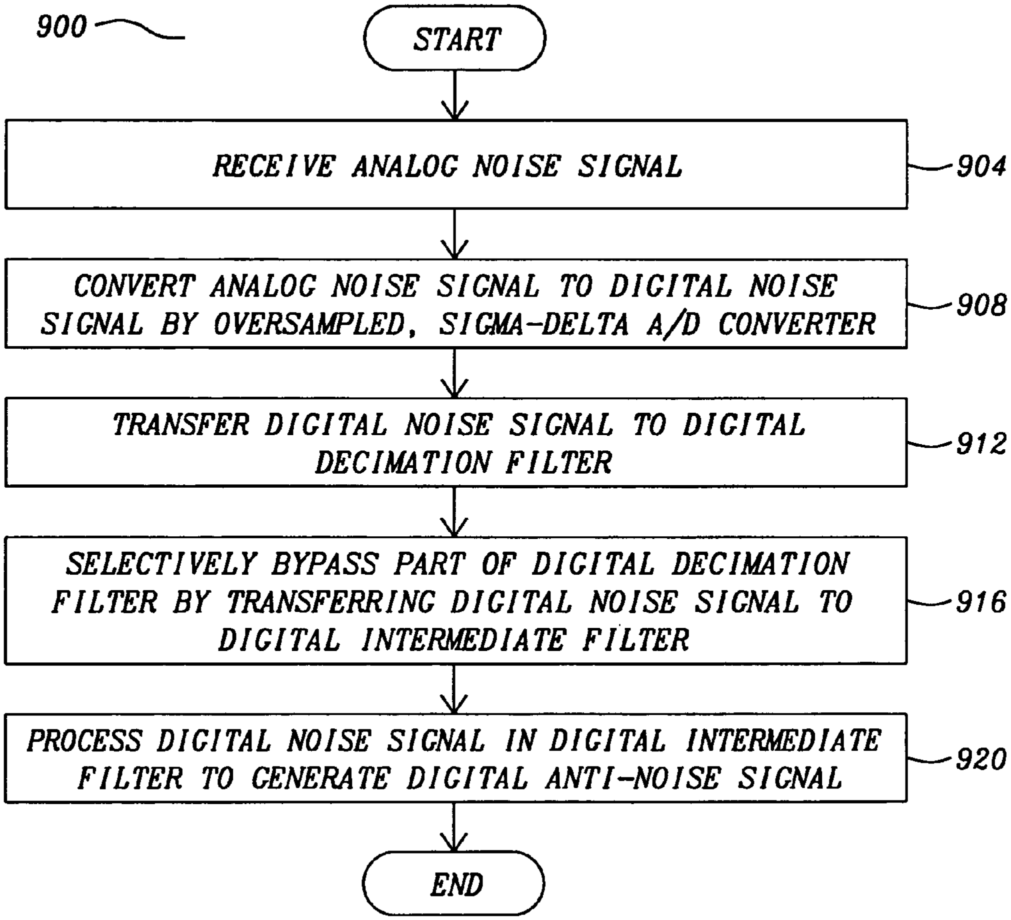
FIG. 9 is a flowchart illustrating one example of a method of digital active noise cancellation in accordance with one embodiment of the invention.

FIG. 9 is a flowchart illustrating one example of a method 900 of digital active noise cancellation in accordance with one embodiment of the invention. The flowchart method 900 shows operating steps performed by an active noise cancellation device employing one example of a method of generating an anti-noise signal for a digital active noise cancellation circuit in a digital audio device. In particular, one example of a method 900 performed by the active noise cancellation device of FIG. 3 is shown. The process begins in step 904 where an analog noise signal 64 is received. In step 908, the analog noise signal 64 is converted to a digital noise signal 261 by an oversampled, sigma-delta A/D converter 204. In step 912, the digital noise signal 261 is transferred into the digital decimation filter 208. In step 916, at least a portion of the digital decimation filter 208 is selectively bypassed 312 by transferring the digital noise signal 261 to the digital intermediate filter 308. Finally, in step 920, the digital noise signal 312 is processed in the digital intermediate filter 308 to generate a digital anti-noise signal 316.

Figure 10:
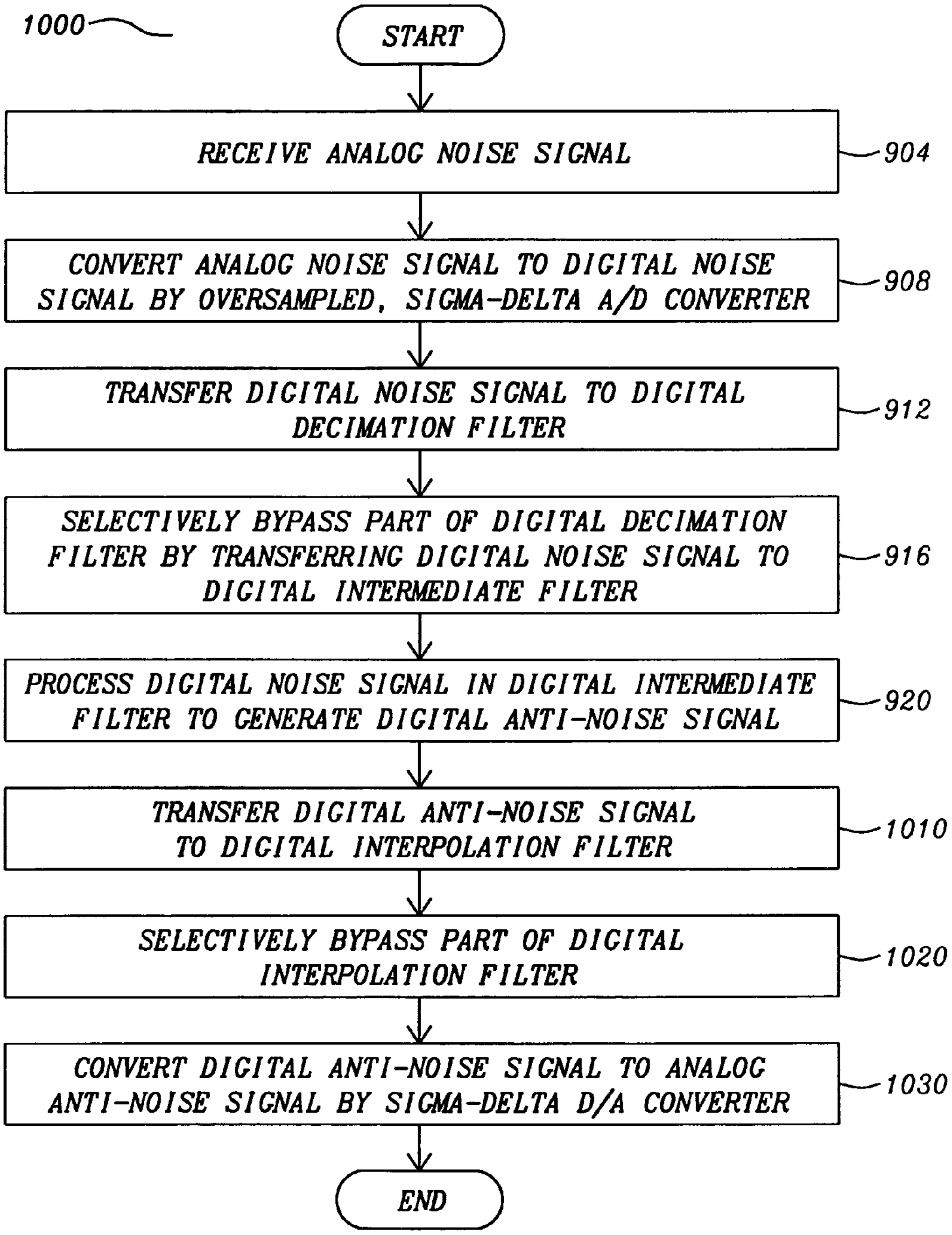
FIG. 10 is a flowchart illustrating one example of a method of digital active noise cancellation in accordance with one embodiment of the invention.

FIG. 10 is a flowchart illustrating one example of a method of digital active noise cancellation in accordance with one embodiment of the invention. The flowchart method 1000 shows the operating steps performed by an active noise cancellation device employing one example of a method of generating an anti-noise signal for a digital active noise cancellation circuit in a digital audio device. In particular, one example of a method 1000 performed by the active noise cancellation device of FIG. 3 is shown. Steps 904-920 are the same as in the method of FIG. 9. In step 1010, the digital anti-noise signal 316 is transferred to the digital interpolation filter 232. In step 1020, a part of the digital interpolation filter 232 is selectively bypassed 316. Finally, in step 1030, the digital anti-noise signal 276 is converted to an analog anti-noise signal 68 by a sigma-delta D/A converter 252.

Figure 11:
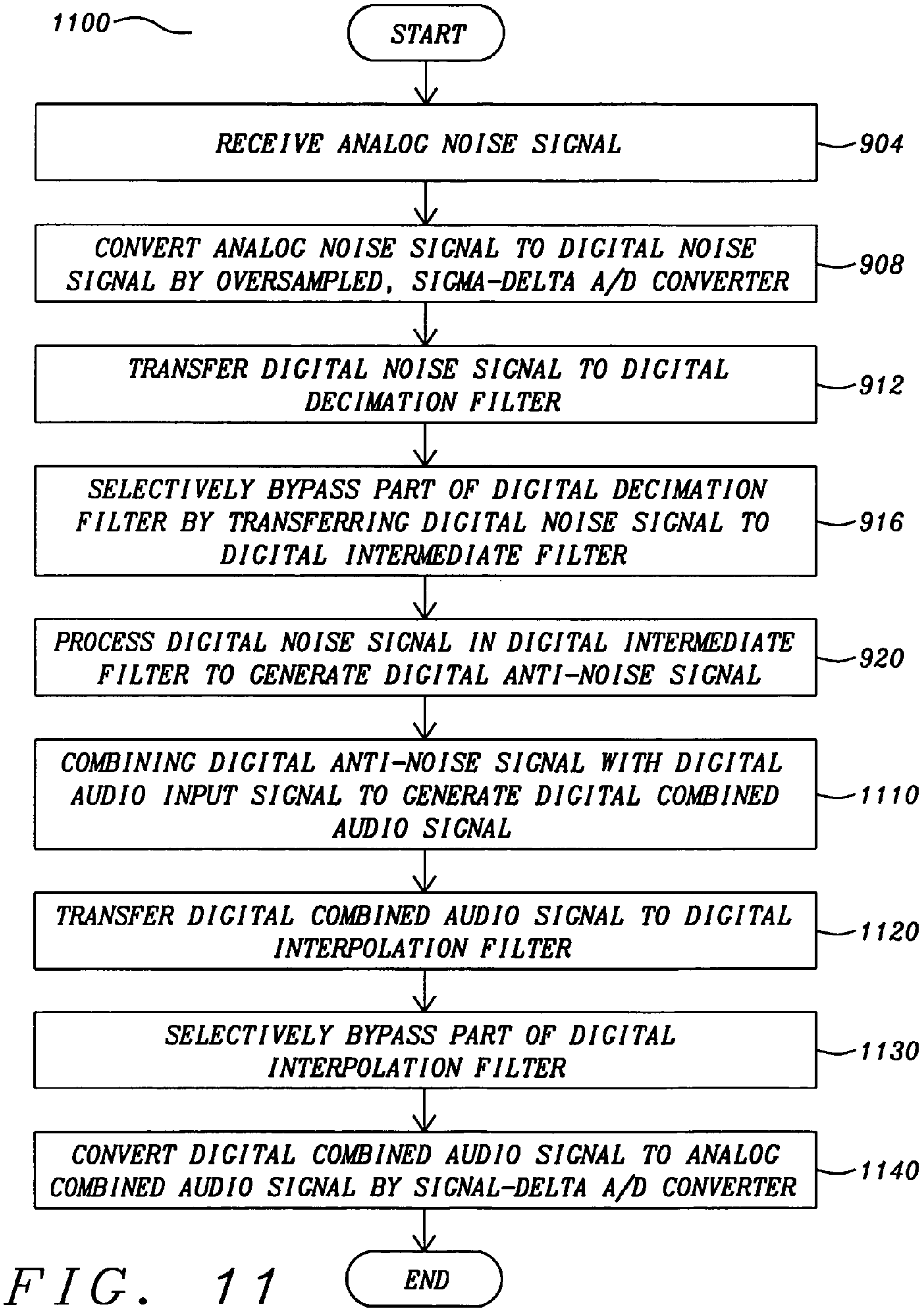
FIG. 11 is a flowchart illustrating one example of a method of digital active noise cancellation in accordance with one embodiment of the invention.

FIG. 11 is a flowchart illustrating one example of a method of digital active noise cancellation in accordance with one embodiment of the invention. The flowchart method 1100 shows the operating steps performed by an active noise cancellation device employing one example of a method of generating an anti-noise signal for a digital active noise cancellation circuit in a digital audio device. In this example, method 1100 performed by the active noise cancellation device of FIG. 2 is shown. This method 1100 shows how the digital anti-noise signal 271, 272, 273, 274, 275, or 276, is combined with a digital audio input signal 74 to generate a digital combined audio signal 68 in the digital intermediate filter 228. Steps 904-920 are the same as in the method of FIG. 9. In step 1110, the digital anti-noise signal is combined with a digital audio input signal to generate a digital combined audio signal. In step 1120, the digital combined audio signal is transferred to the digital interpolation filter 232. In step 1130, a part of the digital interpolation filter 232 is selectively bypassed 316. Finally, in step 1140, the digital combined audio signal is converted to an analog combined audio signal 68 by a sigma-delta D/A converter 252.

The above detailed description of the invention, and the examples described therein, has been presented for the purposes of illustration and description. While the principles of the invention have been described above in connection with a specific device, it is to be clearly understood that this description is made only by way of example and not as a limitation on the scope of the invention.

What is claimed is:

1. A method for generating an anti-noise signal for a digital active noise cancellation circuit in a digital audio device, the method comprising: receiving an analog noise signal; converting the analog noise signal into a digital noise signal by an oversampled, sigma-delta, A/D converter; transferring the digital noise signal to a digital decimation filter operable to down-sample the digital noise signal; selectively bypassing at least a portion of the digital decimation filter by transferring the digital noise signal to a separate digital intermediate filter; and processing the digital noise signal in the digital intermediate filter to generate a digital anti-noise signal.

2. The method of claim 1 further comprising the steps of: transferring the digital anti-noise signal into a digital interpolation filter operable to up-sample the digital anti-noise signal; selectively bypassing at least a portion of the digital interpolation filter; and converting the digital anti-noise signal into an analog anti-noise signal by a sigma-delta, D/A converter.

3. The method of claim 2 wherein the digital noise signal is transferred directly from the A/D converter to the digital intermediate filter and the digital anti-noise signal is transferred directly from the digital intermediate filter to the D/A converter.

4. The method of claim 3 wherein the digital interpolation filter comprises a plurality of FIR filters, an up-sampler, and a sigma-delta modulator.

5. The method of claim 4 wherein the digital noise signal is transferred directly from the A/D converter to the digital intermediate filter and the digital anti-noise signal is transferred directly from the digital intermediate filter to the sigma-delta modulator.

6. The method of claim 4 wherein the digital noise signal is transferred directly from the A/D converter to the digital intermediate filter and the digital anti-noise signal is transferred directly from the digital intermediate filter to the up-sampler.

7. The method of claim 2 wherein the digital decimation filter comprises a CIC filter and a plurality of FIR filters.

8. The method of claim 7 wherein the digital noise signal is transferred from a stage of the CIC filter to the digital intermediate filter and the digital anti-noise signal is transferred directly to the D/A converter.

9. The method of claim 7 wherein the digital noise signal is transferred from one of the FIR filters to the digital intermediate filter and the digital anti-noise signal is transferred directly to the D/A converter.

10. The method of claim 2 wherein the digital interpolation filter comprises a plurality of FIR filters, an up-sampler, and a sigma-delta modulator and wherein the digital decimation filter comprises a CIC filter and a plurality of FIR filters.

11. The method of claim 1 further comprising the steps of: combining the digital anti-noise signal with a digital audio input signal to generate a digital combined audio signal; transferring the digital combined audio signal into a digital interpolation filter operable to up-sample the digital combined audio signal; selectively bypassing at least a portion of the digital interpolation filter; and converting the digital combined audio signal into an analog combined audio signal by a sigma-delta, D/A converter.

12. A digital audio device enabled for active noise cancellation comprising: a digital active noise cancellation circuit operatively coupled to the digital audio circuit comprising: an oversampled, sigma-delta, A/D converter; a digital decimation filter; a separate digital intermediate filter; a digital interpolation filter; and a sigma-delta, D/A converter; wherein the digital active noise cancellation circuit is operative to perform the steps of: receiving the analog noise signal; converting the analog noise signal into a digital noise signal by an oversampled, sigma-delta, analog-to-digital converter; transferring the digital noise signal to a digital decimation filter operable to down-sample the digital noise signal; selectively bypassing at least a portion of the digital decimation filter by transferring the digital noise signal to a digital intermediate filter; and processing the digital anti-noise signal in the digital intermediate filter to generate a digital anti-noise signal; and a digital audio circuit operative to combine an audio signal with an analog anti-noise signal and to amplify the combined signals through a speaker.

13. The device of claim 12 wherein the digital active noise cancellation circuit is further operative to perform the steps of: transferring the digital anti-noise signal into a digital interpolation filter operable to up-sample the digital anti-noise signal; selectively bypassing at least a portion of the digital interpolation filter; and converting the digital anti-noise signal into an analog anti-noise signal by a sigma-delta, D/A converter.

14. The device of claim 13 wherein the digital anti-noise circuit is further operative to transfer the digital noise signal directly from the A/D converter to the digital intermediate filter and to transfer the digital anti-noise signal directly from the digital intermediate filter to the D/A converter.

15. The device of claim 13 wherein the digital interpolation filter comprises a plurality of FIR filters, an up-sampler, and a sigma-delta modulator.

16. The device of claim 15 wherein the digital noise signal is transferred directly from the A/D converter to the digital intermediate filter and the digital anti-noise signal is transferred directly from the digital intermediate filter to the sigma-delta modulator.

17. The device of claim 15 wherein the digital noise signal is transferred directly from the A/D converter to the digital intermediate filter and the digital anti-noise signal is transferred directly from the digital intermediate filter to the up-sampler.

18. The device of claim 13 wherein the digital decimation filter comprises a CIC filter and a plurality of FIR filters.

19. The device of claim 18 wherein the digital noise signal is transferred from a stage of the CIC filter to the digital intermediate filter and the digital anti-noise signal is transferred directly to the D/A converter.

20. The device of claim 18 wherein the digital noise signal is transferred from one of the FIR filters to the digital intermediate filter and the digital anti-noise signal is transferred directly to the D/A converter.

21. The device of claim 13 wherein the digital interpolation filter comprises a plurality of FIR filters, an up-sampler, and a sigma-delta modulator and wherein the digital decimation filter comprises a CIC filter and a plurality of FIR filters.

22. The device of claim 12 wherein the digital active noise cancellation circuit is further operative to perform the steps of: combining the digital anti-noise signal with a digital audio input signal to generate a digital combined audio signal; transferring the digital combined audio signal into a digital interpolation filter operable to up-sample the digital combined audio signal; selectively bypassing at least a portion of the digital interpolation filter; and converting the digital combined audio signal into an analog combined audio signal by a sigma-delta, D/A converter.

23. A digital active noise cancellation circuit device comprising: an oversampled, sigma-delta, A/D converter; a digital decimation filter; a separate digital intermediate filter; a digital interpolation filter; and a sigma-delta, D/A converter; wherein the digital active-noise cancellation circuit device is operative to perform the steps of: receiving the analog noise signal; converting the analog noise signal into a digital noise signal by an oversampled, sigma-delta, analog-to-digital converter; transferring the digital noise signal to a digital decimation filter operable to down-sample the digital noise signal; selectively bypassing at least a portion of the digital decimation filter by transferring the digital noise signal to a digital intermediate filter; and processing the digital noise signal in the digital intermediate filter to generate a digital anti-noise signal.

24. The device of claim 23 wherein the digital active noise cancellation circuit device is further operative to perform the steps of: transferring the digital anti-noise signal into a digital interpolation filter operable to up-sample the digital anti-noise signal; selectively bypassing at least a portion of the digital interpolation filter; and converting the digital anti-noise signal into an analog anti-noise signal by a sigma-delta, D/A converter.

25. The device of claim 24 wherein the digital anti-noise circuit is further operative to transfer the digital noise signal directly from the A/D converter to the digital intermediate filter and to transfer the digital anti-noise signal directly from the digital intermediate filter to the D/A converter.

26. The device of claim 24 wherein the digital interpolation filter comprises a plurality of FIR filters, an up-sampler, and a sigma-delta modulator.

27. The device of claim 26 wherein the digital noise signal is transferred directly from the A/D converter to the digital intermediate filter and the digital anti-noise signal is transferred directly from the digital intermediate filter to the sigma-delta modulator.

28. The device of claim 26 wherein the digital noise signal is transferred directly from the A/D converter to the digital intermediate filter and the digital anti-noise signal is transferred directly from the digital intermediate filter to the up-sampler.

29. The device of claim 24 wherein the digital decimation filter comprises a CIC filter and a plurality of FIR filters.

30. The device of claim 24 wherein the digital interpolation filter comprises a plurality of FIR filters, an up-sampler, and a sigma-delta modulator and wherein the digital decimation filter comprises a CIC filter and a plurality of FIR filters.

31. The device of claim 23 wherein the digital active noise cancellation circuit device is further operative to perform the steps of: combining the digital anti-noise signal with a digital audio input signal to generate a digital combined audio signal; transferring the digital combined audio signal into a digital interpolation filter operable to up-sample the digital combined audio signal; selectively bypassing at least a portion of the digital interpolation filter; and converting the digital combined audio signal into an analog combined audio signal by a sigma-delta, D/A converter.

* * * * *